United States Patent [19]
Seltzer

[11] Patent Number: 5,908,566
[45] Date of Patent: Jun. 1, 1999

[54] MODIFIED PLASMA TORCH DESIGN FOR INTRODUCING SAMPLE AIR INTO INDUCTIVELY COUPLED PLASMA

[75] Inventor: Michael D. Seltzer, Ridgecrest, Calif.

[73] Assignee: The United States of America as represented by the Secretary of the Navy, Washington, D.C.

[21] Appl. No.: 08/932,397

[22] Filed: Sep. 17, 1997

Related U.S. Application Data

[63] Continuation-in-part of application No. 08/932,023, Sep. 17, 1997, application No. 08/932,401, Sep. 17, 1997, and application No. 08/932,233, Sep. 17, 1997, Pat. No. 5,834,656.

[51] Int. Cl.$^6$ .................................................. B23K 10/00
[52] U.S. Cl. ............................... 219/121.52; 219/121.51; 219/121.36; 219/121.48; 315/111.51
[58] Field of Search ............... 219/121.52, 121.48, 219/121.51, 121.37, 121.36; 315/111.31, 111.51; 313/231.31, 231.41; 110/246, 346

[56] References Cited

U.S. PATENT DOCUMENTS

| | | |
|---|---|---|
| 29,304 | 7/1860 | Greenfield et al. . |
| 3,296,410 | 1/1967 | Hedger .................................. 219/121.52 |
| 3,965,747 | 6/1976 | McCorkle . |
| 3,965,748 | 6/1976 | Boubel et al. . |
| 4,091,835 | 5/1978 | Frampton . |
| 4,159,635 | 7/1979 | Sehmel . |
| 4,293,220 | 10/1981 | Denton et al. . |
| 4,390,772 | 6/1983 | Hiratake . |
| 4,482,246 | 11/1984 | Meyer et al. . |
| 4,551,609 | 11/1985 | Falk .................................... 219/121.52 |
| 4,566,342 | 1/1986 | Kurz . |
| 4,575,609 | 3/1986 | Fassell et al. ...................... 315/111.51 |
| 4,649,760 | 3/1987 | Wedding . |
| 4,739,147 | 4/1988 | Meyer et al. . |
| 5,012,065 | 4/1991 | Rayson et al. . |
| 5,090,257 | 2/1992 | Bruce . |
| 5,233,156 | 8/1993 | Chan et al. .......................... 315/111.51 |
| 5,479,254 | 12/1995 | Woskov et al. . |
| 5,526,110 | 6/1996 | Braymen . |

OTHER PUBLICATIONS

J.D. Chase Theoretical and Experimental Investigation of Pressure and Flow in Induction Plasmas, Journal of Applied Physics, Nov. 1971 vol. 42, No. 12, pp. 4870–4879.

D. Truitt & J.W. Robinson Spectoscopic Studies of Organic Compounds Introduced into a Radio Frequency Induced Plasma. Analytica Chemica Acta, 51–1970 pp. 61–67 Elsevier Publishing Company, Amsterdam.

Seltzer, Michael D. An Argon ICP–Based Continuous Emissions Monitor for Hazardous Air Pollutant Metals: Field Demonstration Presentation of the Ari Waste Managment Association. 90$^{th}$ Annual Management Exhibition.

(List continued on next page.)

*Primary Examiner*—Mark Paschall
*Attorney, Agent, or Firm*—Gregory M. Bokar; David S. Kalmbaugh

[57] ABSTRACT

A plasma torch for reliable analysis of airborne particulate matter permits real-time monitoring of airborne metal pollutants in flue gases from furnaces and incinerators. The torch injects sample air into argon plasma and has an outer tube to confine plasma gas for generating a plasma fireball. An intermediate tube has an outwardly flared portion concentrically disposed within the outer tube to form an outer annulus for feeding plasma gas to the fireball. The intermediate tube also has an injector sheath tube joined at its base to the base of the flared portion and concentrically disposed within the flared portion. The injector sheath tube is parallel to the outer tube. An inner capillary injector tube injects sample air into the plasma fireball. The inner capillary injector tube is concentrically disposed within the injector sheath tube to form an inner annulus that directs annular flow of auxiliary gas to alter the surface of the central region of the plasma fireball and channels the sample air to inject it through the surface and into the plasma fireball. The annular flow of auxiliary gas assures injection of the sample air at velocities which preserve residence time of the sample air to effect efficient vaporization and excitation of the metals.

7 Claims, 2 Drawing Sheets

OTHER PUBLICATIONS

Seltzer, Michael D. An Inductively Coupled Argon Plasma Continous Emissions Monitor forHazardous Air Pollutant Metals, Enviromental Science and Technology Sep. 1997. Submitted Apr. 1997.

Seltzer, Michael D & Gerhard A. Meyer, Keeping and Eye on Metals Emmisions, Enviromental Protection, Jun. 1997 vol. 8 No. 6—pp. 26–29.

Seltzer, Michael D. Continous Air Monitoring Using Inductively Coupled Plasma, Applied Spectorscopy, Submitted Jun. 1997.

Emmisions Measurment Branch, nsps Test Method, EMTIC M–002 Technical Support Division OAQPS, EPA, NAWS China Lake.

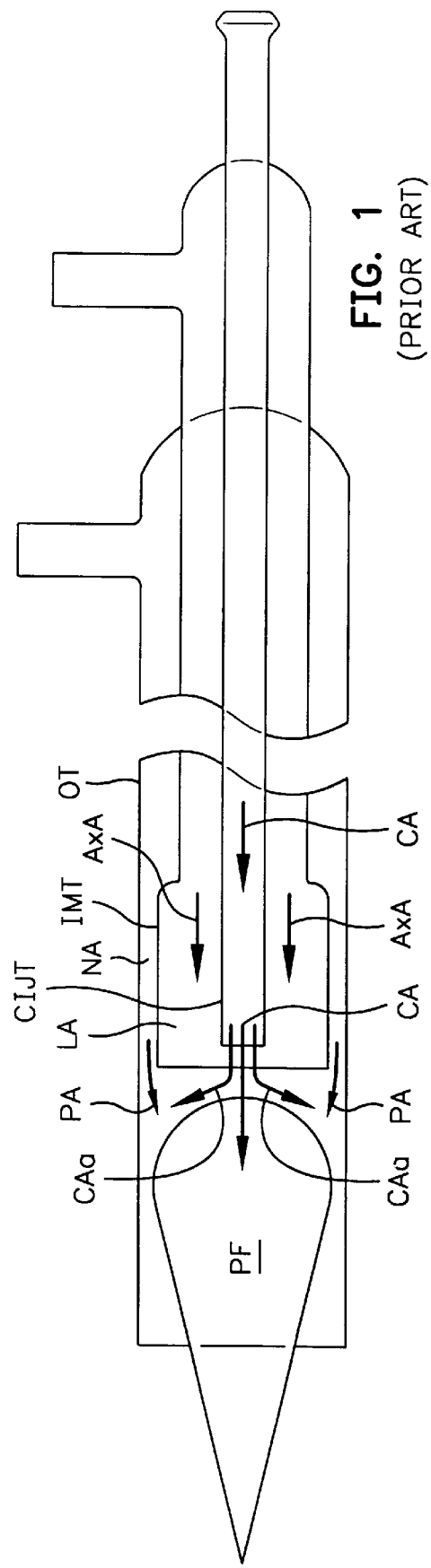
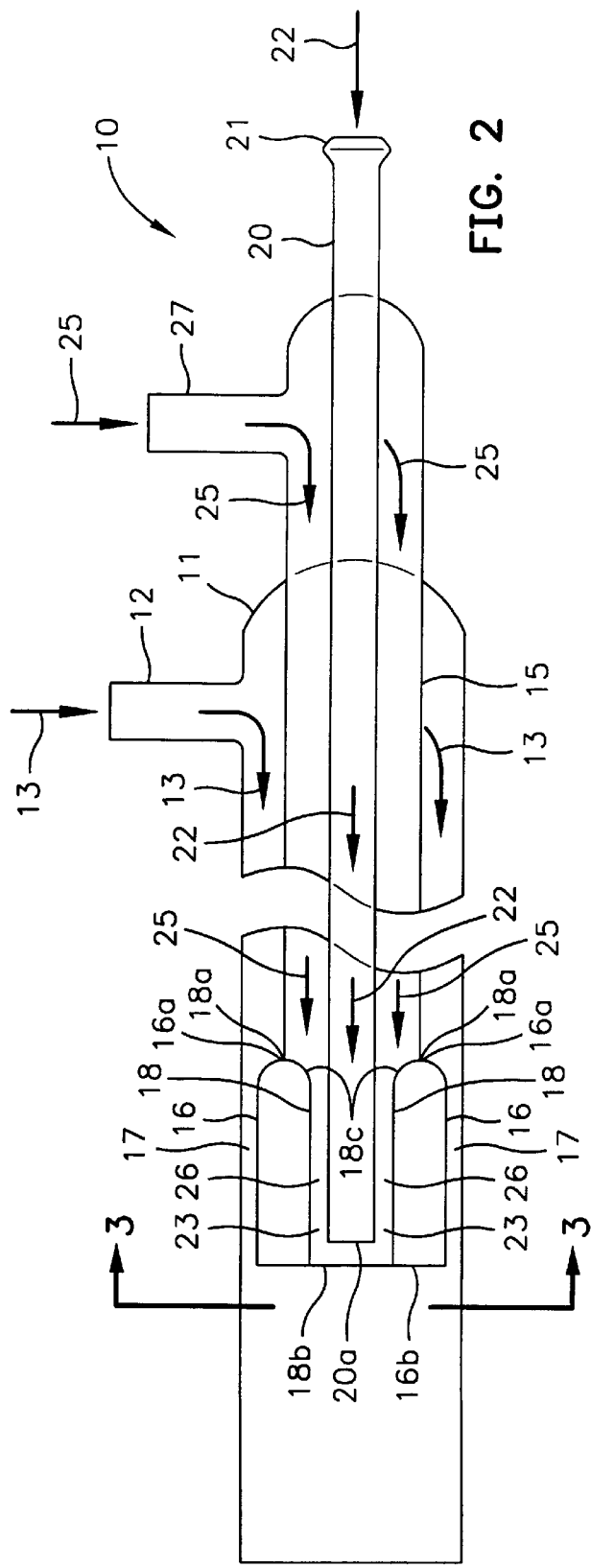

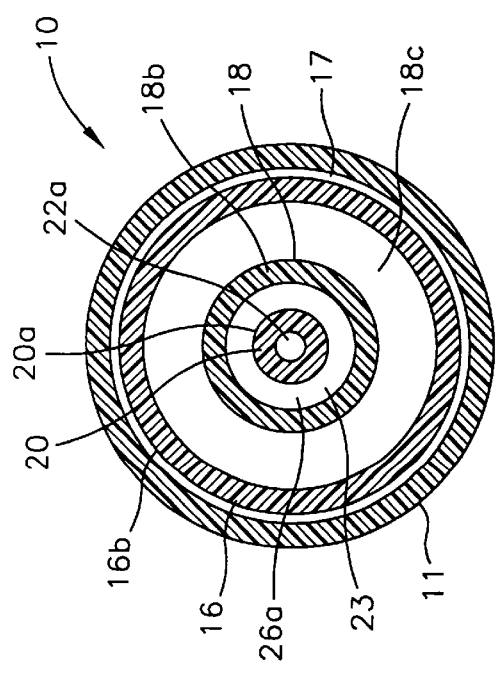
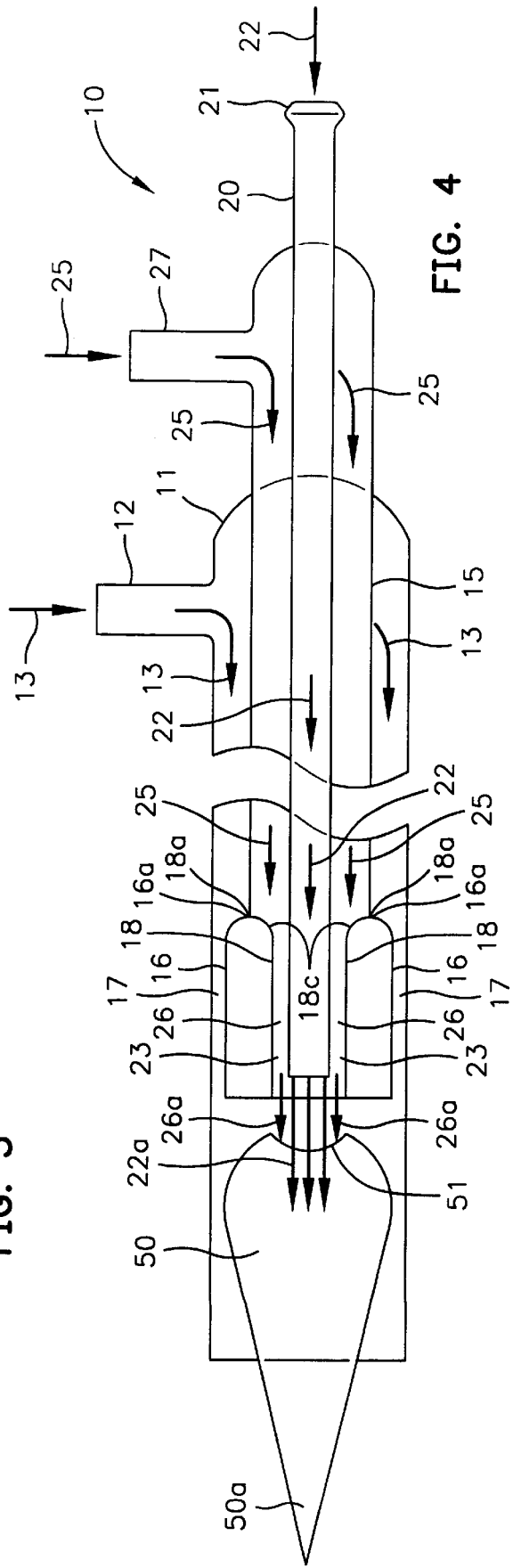

MODIFIED PLASMA TORCH DESIGN FOR INTRODUCING SAMPLE AIR INTO INDUCTIVELY COUPLED PLASMA

CROSS REFERENCE TO RELATED APPLICATIONS

This is a continuation in part of U.S. patent applications entitled "Correction of Spectral Interferences Arising from CN Emission in Continuous Air Monitoring Using Inductively Coupled Plasma Atomic Emission Spectrometry" by Michael Seltzer. U.S. Patent and Trademark Office Ser. No. 08/932,023, Navy Case No. 77871, filed Sep. 17, 1997 now pending and "Method and Apparatus for Automated Isokinetic Sampling of Combustor Flue Gases for Continuous Monitoring of Hazardous Metal Emissions" by Michael Seltzer, U.S. Patent and Trademark Office Ser. No. 08/932, 401, Navy Case No. 78564, filed Sep. 17, 1997 now allowed and "Sampling Interface for Continuous Monitoring of Emissions" by Michael Seltzer, U.S. Patent and Trademark Office Ser. No. 08/932,233, Navy Case No. 78274, filed Sep. 17, 1997 now U.S. Pat. No. 5,834,656 incorporates all references and information thereof by reference herein.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to plasma torches used for spectrochemical analysis. In particular, this invention relates to a plasma torch designed to analyze samples of air in an inductively coupled plasma.

Plasma torches, since their inception in the early 1970s, have been designed expressly for use with plasma gases of homogeneous composition. This is in contrast to the invention to be described hereinbelow which involves the introduction of sample air into argon plasma. Consequently, the design of these prior art torches has been optimized for homogeneous gases, primarily, because the prior art has not recognized the need to introduce air into argon plasma, see, for example, U.S. Reissue Pat. RE 29,304. Since argon inductively coupled plasmas are used exclusively for the elemental analysis of liquid samples such as water, and maximum sensitivity is often required, it has been found that the addition of other gases typically degrades analytical performance. Consequently, the introduction of air into argon plasmas has been avoided and the absence of this requirement until now has left the problems associated with air introduction unsolved.

Referring to FIG. 1, typical prior art plasma torch T consists of three concentric quartz tubes that are fused or otherwise held together using appropriate hardware. These tubes are commonly called outer tube OT, tulip-shaped intermediate tube IMT and central injector tube CIJT. Three distinct argon streams flow through these tubes. Typically, through narrow annulus NA formed between outer tube OT and tulip-shaped intermediate tube IMT, plasma argon PA flows at rates of 15–20 liters per minute. In the large annulus LA located between intermediate tube IMT and central injector tube CIJT, auxiliary argon AXA typically flows at 0–2 liters per minute. Carrier or aerosol argon CA flows at 0.5–1 liter per minute through central injector tube CIJT.

The narrow annulus NA in this classic torch geometry that was formed between tulip-shaped intermediate tube IMT and outer tube OT adequately provided a suitable flow of plasma gas PA. However, the velocity of auxiliary argon AXA through the area inside of the "tulip" has been found to be insufficient to promote satisfactory injection of sample air with carrier aerosol CA into plasma fireball PF and produce accurate results or avoid damaging the tubes. The state-of-the-art torches have had great difficulty when air flow of approximately 0.5 liters per minute is added to the flow of argon carrier CA through carrier injector tube CIJT since some portion CAa of carrier CA would inadvertently flow around the fireball. The geometry of standard plasma torches makes air injection difficult to achieve under analytically-favorable conditions, and failure to achieve air injection leads to accelerated aging of these torches.

Thus, in accordance with this inventive concept, a need has been recognized in the state of the art for plasma torches that provide reliable analyses of airborne samples.

SUMMARY OF THE INVENTION

The present invention is directed to providing a plasma torch for airborne particulate matter. The plasma torch has an outer tube to confine plasma gas for generating a plasma fireball. An intermediate tube has an outwardly flared portion concentrically disposed within the outer tube to form an outer annulus for feeding the plasma gas to the plasma fireball. The intermediate tube also has an injector sheath tube joined at its base to the base of the flared portion and concentrically disposed within it. The injector sheath tube is parallel to the outer tube. An inner capillary tube injects sample air into the plasma fireball and is concentrically disposed within the injector sheath tube to form an inner annulus. The inner annulus directs the annular flow of an auxiliary gas such as argon plasma gas to the central region of the plasma fireball and channels the sample air into the plasma fireball.

An object is to provide a plasma torch for analysis of elements.

Another object is to provide a plasma torch for analysis of airborne particulate matter.

Another object is to provide a plasma torch for real-time monitoring of airborne metal pollutants.

Another object is to provide a plasma torch for real-time monitoring of airborne metal pollutants in flue gases from furnaces and incinerators to promote pollution prevention and to ensure continuous compliance with environmental regulatory requirements.

Still another object is to provide to provide a plasma torch that injects sample air into argon plasma for detecting airborne metals.

Still another object is to provide to provide a plasma torch that avoids the problems associated with analysis of a sample air stream.

Another object is to provide a plasma torch that injects sample air into argon plasma at velocities that are favorable for sensitive detection of airborne metals.

An object of the invention is to provide a plasma torch that allows sufficient residence time for airborne metals in the plasma for efficient vaporization and excitation of the metals.

Another object is to provide a plasma torch having an injector sheath tube to focus auxiliary argon flow onto the central region of the plasma fireball to alter the shape of the fireball's surface to facilitate penetration of the sample air stream into the fireball.

Another object is to provide an argon torch permitting efficient introduction of sample air into argon plasma to provide desired analytical performance while protecting the quartz torch from rapid thermal degradation caused by air transferring from the plasma.

These and other objects of the invention will become more readily apparent from the ensuing specification when taken in conjunction with the appended claims.

BRIEF DESCRIPTION OF THE DRAWINGS

FIG. 1 is a cross-sectional side view of a classical plasma torch of the prior art.

FIG. 2 is a cross-sectional side view of the plasma torch in accordance with this invention.

FIG. 3 is a cross-sectional end view of the plasma torch of this invention taken generally along lines 3—3 in FIG. 2 and showing exaggerated cross-sectional dimensions with respect to the other figures.

FIG. 4 is a cross-sectional side view of the plasma torch in accordance with this invention showing injection of the sample air into the plasma fireball through the altered surface of the fireball.

DESCRIPTION OF THE PREFERRED EMBODIMENT

A recent development has recently focussed attention on instrumentation and methodology for real-time monitoring of airborne metal pollutants, see U.S. Pat. No. 5,596,405. A sample stream of air is injected directly into an inductively coupled argon plasma and airborne metals are vaporized and excited resulting in emission of characteristic wavelengths of light. Inductively coupled plasma is sustained by flowing argon through a quartz plasma torch positioned axially within a helical, radio frequency induction coil. Injection of air into the argon plasma his been accomplished with some difficulty and somewhat satisfactory results have been obtained.

However, in accordance with this invention, two serious problems have been noted that require an examination of the process of air injection into argon plasma an optimization of this process. Because of differences in thermal and electrical properties of argon and air (nitrogen, oxygen), and certain hydrodynamic properties of the argon plasma, injection of the sample air stream cannot be achieved unless the velocity of the air stream is sufficiently high to overcome a phenomenon known as magnetohydrodynamic thrust, see J. D. Chase, "Theoretical and Experimental Investigations of Pressure and Flow on Induction Plasmas," *J. Appl. Physics*, 42 (1971) 4870–4879. (When a stream of argon is injected into the argon plasma in a conventional torch, adequate penetration in the plasma fireball is achieved with considerable ease and at much lower velocities.) Unfortunately, at the velocities required to achieve penetration of the argon plasma with an air stream, airborne metals entrained in the sample air stream are not given sufficient residence time in the plasma to undergo adequate vaporization and excitation to promote sensitive detection.

Consequently, in accordance with this invention, it has been recognized that the potential sensitivity of this approach has not been entirely realized. Secondly, using a conventional plasma torch, the air is not injected in its entirety through the argon plasma. Instead, most of it is forced, or deflected, to flow around the outside of the argon plasma. Air has much higher thermal conductivity than pure argon Thus, considerable heat transfer occurs between the hot argon plasma and the quartz torch used to sustain the plasma. Under normal circumstances, when pure argon plasma is operated, little heat transfer to quartz tubes occurs, and torches are spared thermal degradation resulting in hundreds of hours of useful operation. In accordance with this invention, it has been discovered that where a sample air stream is introduced into argon plasma there is overheating of a conventional plasma torch due to inadequate penetration of the argon plasma by the air stream. This results not only in pronounced degradation of analytical performance but creates de-vitrification of the quartz and accelerated aging of the conventional torch resulting in useful operating lifetimes of less than 20 hours.

Therefore, this invention provides a plasma torch design that makes it more amenable to the introduction of a sample air stream. The invention promotes improved penetration of the air stream into the argon plasma resulting in enhanced sensitivity for airborne metal detection and protection of the quartz plasma torch from thermal degradation. As a consequence, the lifetime of the torch of this invention is extended at least tenfold resulting a direct cost savings.

Referring to FIGS. 2, 3, and 4 of the drawings, plasma torch 10 has outer tube 11 provided with fitting 12 for introducing argon plasma gas 13. Gas inlet fitting 12 is mounted tangentially on tube 11 to induce a tangential flow of plasma gas 13 within outer tube 11. This tangential flow component of the plasma gas has been found to be advantageous for this plasma torch design. Typically, outer tube 11 has an outer diameter of about 20 mm and an inner diameter of about 18 mm.

An intermediate tube 15 is concentrically disposed within tube 11 and has concentrically disposed outwardly flared portion, or "tulip" 16 that defines outer annulus 17 between it and the inner surface of outer tube 11. Typical dimensions for the outer diameter of portion 16 are about 17 mm and inner diameter of about 15 mm. An annular flow of plasma gas 13a is fed through annulus 17 to feed and sustain plasma fireball 50 and tail flame 50a. The plasma is inductively coupled to an induction coil, not shown, and the coil is driven by a suitable radio frequency energy source to sustain the plasma fireball according to procedures well known in the art.

Intermediate tube 15 is also provided with injector sheath tube 18. Injector sheath tube 18 is joined at its base 18a to base 16a of flared portion 16. The bases can be joined in a variety of ways either during formation by the glass blower or the bases can be fused or appropriately fitted later. Whatever fabrication technique is selected, injector sheath tube 18 is concentrically disposed within flared portion 16 and is parallel with outer tube 11. Injector sheath tube 18 has an outer diameter of about 9 mm and an inner diameter of 7 mm.

Inner capillary injector tube 20 is concentrically disposed within injector sheath tube 18 and is provided with gas inlet fitting 21 to receive sample air 22 in tube 20 and inject it as sample air stream 22a into fireball 50. Sample air 22 contains mixed air (nitrogen, oxygen), argon and air-entrained materials, such as metals or other constituents of interest. The air and air entrained materials in sample air 22 can be taken from flue gases containing airborne metal pollutants from furnaces and incinerators or can be air from an area containing hazardous chemicals, etc. Predetermined amounts of argon are mixed with the other constituents to facilitate injection in plasma fireball 50.

Inner capillary injector tube 20 has an outer diameter of about 4 mm and an inner diameter of about 1.5 mm and receives sample air 22 and injects sample air stream 22a through end 20a. The outer surface of inner capillary tube 20 forms a 1.5 mm thick inner annulus 23 between the inside of injector sheath tube 18 and it, to pass and direct an annular flow 26 of auxiliary gas 25 to central region 51 of plasma fireball 50.

Auxiliary gas 25 is argon introduced into intermediate tube 15 via gas inlet fitting 27. Fitting 27 is mounted perpendicularly on intermediate tube 15 to direct the flow of auxiliary gas 25 toward the longitudinal axis of intermediate tube 15. Locating fitting in such a manner eliminates swirling or tangential motion of the auxiliary argon so that it can more readily accomplish its intended function. Annular flow 26 forms a concentric sheath flow 26a toward and onto central region 51. Flow 26a alters the shape of central region 51, allows penetration of sample air into plasma fireball 50, and channels sample air 22a onto and into the fireball.

Plasma torch 10 includes injector sheath tube 18 around inner capillary injector tube 20 to create a concentric 'sheath flow' 26*a* of auxiliary argon 25 around the injected sample air stream 22*a*. This capability is a marked difference from the prior art standard torch mentioned above that has the flow of argon through the enlarged portion of the intermediate tube that surrounds the injector tube. Under operating conditions where pure argon plasma is sustained, the arrangement of the prior art torch does facilitate penetration of aerosol into the plasma fireball by modifying the bottom of the fireball.

However, the prior art approach is not nearly as effective where an air stream is to be injected into the fireball. To achieve partial effectiveness in this prior art torch, auxiliary argon must flow through the intermediate tube at volume levels, or mass flow-rates approaching those that are sufficient to extinguish the plasma.

Contrary to the prior art torch, plasma torch 10 additionally has injector sheath tube 18 that measures about 9 mm outer diameter and about 7 mm inner diameter. Injector sheath tube 18 concentrically surrounds inner capillary tube 20 (outer diameter about 4 mm) and extends at its end 18*b* to about 3 mm beyond end 20*a* of inner capillary tube 20. This arrangement creates a high velocity argon sheath flow 26*a* of auxiliary gas 25 that facilitates penetration of injected air stream 22*a* into plasma fireball 50 and, simultaneously, prevents flow of injected sample air stream 22*a* around fireball 50. This helps minimize thermal degradation of the tulip of intermediate tube 16. Therefore, by reducing the cross-sectional area, or thickness, of inner annulus 23 to about 1.5 mm, annular flow 26 of auxiliary argon 25 flows with dramatically increased flow velocity and also is more focussed in sheath flow 26*a*. The desired penetration of plasma fireball 50 is achieved without requiring mass flow rates, or volumes, that threaten to extinguish the plasma.

Thus, relatively high velocity argon sheath flow 26*a* of auxiliary argon essentially alters the surface of plasma fireball 50 thereby facilitating penetration of injected sample air stream 22*a*. Injection of air thereby is accomplished using flow velocities of the sample air that allow favorable residence times for the sample air in the plasma. This results in satisfactory analytical performance.

The constituents of plasma torch 10 are made from a variety of appropriately sized sections of quartz tubing or any other workable, high refractory material (ceramics) capable of withstanding the temperatures and energies associated with inductively coupled plasmas. Furthermore, the fabrication techniques for the novel structure of plasma torch 10 are chosen from a number of widely used proven procedures to produce a plasma torch that will give prolonged useful service.

Accordingly, plasma torch 10 can be fabricated by properly equipped, competent glassblowers. To create the sheath argon flow described above, a quartz tube (injector sheath tube 18) is located concentrically around inner capillary tube 20 as shown in FIGS. 2, 3, and 4. Injector sheath tube 18 can be added at the time of fabrication and should be done so in a manner that the original geometry of the standard torch is not changed. The 'tulip' shape of flared portion 16 of intermediate tube 15 is preserved to ensure proper operation. Injector sheath tube 18 may be regarded as an extension of the 'stem' of the 'tulip'. The actual diameter of injector sheath tube 18 may vary; but to ensure maximum effectiveness, inner annulus 23 between injector sheath tube 18 and inner capillary injector tube 20 should not exceed 1.5 mm. As mentioned above, if the tip of inner capillary injector tube 20 has an outer diameter of 4 mm then the inner diameter of injector sheath tube 18 should be no larger than 7 mm. Since the inner diameter of the 'tulip stem' portion of intermediate tube 15 is typically 10 mm, a tapered transition or interface 18*c* will be required to join injector sheath tube 18 to the 'tulip stem'. This interface 18*c* is shown in the region that includes ends 16*a* and 18*a* of flared portion 16 and injector sheath tube 18, respectively. It is absolutely essential that all quartz tubes used in torch fabrication are aligned and made concentric in the final steps of manufacture.

As an alternative to permanently affixing injector sheath tube 18 to intermediate tube 15, a demountable arrangement can be configured in which the halves of a tapered ground joint can be fashioned on the end of injector sheath tube 18 and on the inside of the 'tulip stem', respectively. This would be similar to technology described in U.S. Pat. No. 4,739,147.

Irrespective which fabrication approach is selected, end 18*b* of injector sheath tube 18 extends to the same level as end 16*b* of flared portion 16 (tulip) of intermediate tube 15. End 20*a* of inner capillary injector tube 20 is recessed up to 3 mm back from the ends 18*b* and 16*b* of injector sheath tube 18 and flared portion 16, respectively.

Addition of injector sheath tube 20 allows focusing flow sheath 26*a* of auxiliary argon flow 26, resulting in a concave indentation, or at the very least, flattening of the argon plasma fireball 50. This greatly facilitates injection of sample air stream 22*a* into argon plasma fireball 50 in a manner that retains desired analytical properties of the argon plasma and, simultaneously, protects the components of torch 10 from thermal damage caused by undesirable flow of air around fireball 50.

Torch 10 fabricated in accordance with this invention is able to inject sample air 21 into argon plasma fireball 50 at velocities that are favorable for sensitive detection of airborne metals. The airborne particulate matter containing the metals thereby has sufficient residence time in the plasma fireball to effect efficient vaporization and excitation of the metals.

Prior to this invention analysis of air samples was difficult since the electrical and thermal differences between plasma gas (argon) and sample gas (air) made the injection process difficult. The argon plasma fireball in prior art torches resisted penetration by the injected air stream and diverted most of it around the fireball. This resulted in poor, if any, excitation of airborne metals and inadvertent damage to the quartz torch tubing due to the relatively high thermal conductivity of air.

The present invention recognizes and addresses these problems of the prior art by introducing what may be the only significant modification of the classic plasma torch design in years! The addition of injector sheath tube 20 allows auxiliary argon flow 26 to be focused into an argon sheath flow 26a that impinges central region 51 of plasma fireball 50 in a fashion that alters the shape of the fireball's surface and facilitates penetration of sample air stream 22a into fireball 50. Thus, the invention permits injection of sample air into argon plasma for detecting airborne metals in a revolutionary application of technology. This innovation permits efficient introduction of sample air into argon plasma while maintaining desired analytical performance and, at the same time, protecting the quartz torch from rapid thermal degradation caused by the presence of air in the plasma.

Representative operational parameters of torch 10 are:

| Function | Range | Optimum |
| --- | --- | --- |
| plasma gas 13 | 15–17 1/min. argon | 16 1/min. argon |
| Aux. gas flow 26 argon | 0.7–0.9 1/min. argon | 0.85 1/min. |
| Sample air stream 22a | 0.3–0.6 1/min. sample air plus 0.1–0.2 1/min. argon | 0.45 1/min. sample air plus 0.15 1/min. argon |

It is emphasized that the dimensions of injector sheath tube 18 and inner capillary injector tube 20 are critical since they define the size of inner annulus 23 formed between them. In accordance with this invention preferably torch 10 is fabricated with inner annulus 23 having a thickness of not greater than 1.5 mm. This assures that torch 10 creates argon sheath flow 26a to alter central surface 51 of argon plasma fireball 50 and to make it more amenable to penetration by sample air stream 22a. In other words, injector sheath tube 18 in torch 10 is responsible for the creation of the appropriate gas velocity that shapes a concave indentation or flattening of plasma fireball 50 to facilitate injection of sample air stream 22a at velocities sufficiently low to retain sufficient sample residence time in plasma fireball 50. In contradistinction, the prior art torch does not have injector sheath tube 18. This necessitates injection of sample air at much higher mass flow velocities; however, at these higher mass flow velocities, sample residence times are too short for optimum analytical performance. Similarly, a prior art torch that does not have injector sheath tube 18 may have to dramatically increase the auxiliary argon flow to attempt to improve penetration of the plasma fireball by sample air; however, at the high auxiliary argon flows required, the plasma becomes unstable and is easily extinguished.

In accordance with this invention, when the inner capillary injector tube 20 has a 4 mm outer diameter the injector sheath tube 18 should have an inner diameter of 7 mm to create an annulus of 1.5 mm. An auxiliary argon flow range of 0.7–0.9 liters per minute fed through this annulus makes a focused sheath flow velocity range of 45–58 centimeters per second.

If the inner diameter of injector sheath tube 18 were to be increased, a proportional increase in auxiliary argon flow 26 would be required to provide the same sheath flow velocity. However, care must be exercised since increased mass flow of argon may have deleterious effects on plasma fireball 50. This is because increased mass flows of auxiliary argon may be high enough to lift or otherwise displace plasma fireball. This is a serious problem since the fireball may be lifted to the extent that interaction with the radio frequency load coil that supplies energy to the plasma will be decreased and the plasma could be extinguished.

If, on the other hand, injector sheath tube 18 were to be decreased to an inner diameter smaller than 7 mm, a proportional decrease of auxiliary argon flow would be required to provide the same sheath flow velocity. In this case, the decreased mass flow of argon would definitely have deleterious effects on the analytical performance of the plasma.

Therefore, torch 10 has inner capillary injector tube 20 with a 4 mm outer diameter and injector sheath tube 18 with an inner diameter of 7 mm to provide the suitable gas velocities at the volumetric flow rates listed above.

Although torch 10 has been described as being fabricated from materials which accommodate argon within described flow rates, it is to be understood that other torch configurations, gases, and flow rates could be selected having the teachings of this invention in mind. The exact configuration of torch 10 is decided by the requirements of the job at hand. Therefore, it is to be understood that, having the teachings of this invention in hand, one skilled in the art to which this invention pertains could configure the plasma torch of this invention differently, and still be within the scope of this inventive concept. This selection of other known materials to meet other analysis requirements is well within the purview of one skilled in the art in view of the teachings of this invention.

Therefore, it should be readily understood that many modifications and variations of the present invention are possible within the purview of the claimed invention. It is to be understood that within the scope of the appended claims the invention may be practiced otherwise than as specifically described.

I claim:

1. An inductively coupled plasma torch for exciting a chemical element to emit electromagnetic radiation, said plasma torch having an outer tube, an inner tube coaxial therewith, an axially disposed capillary tube, a first feed line for conveying argon plasma gas, a second feed line for conveying argon cooling gas and a third feed line for conveying a sample argon gas;

said sample argon gas includes a suspended aerosol said aerosol containing chemical elements to be excited;

said plasma torch is mounted coaxially within an energized induction coil;

said argon cooling gas is caused to flow through said plasma torch;

a plasma fireball is sustained within the confines of said outer tube and above said inner tube;

said argon sample gas is introduced through said capillary tube penetrating said plasma fireball such that said aerosol traverses central portion of said plasma fireball to achieve maximum excitation;

said argon plasma gas conveyed by said first feed line and flowing through the wide space between said inner tube and said capillary tube is not essential for sustaining said plasma fireball, but is useful for lifting said plasma fireball to prevent melting of said capillary tube and to prevent the formation of carbon deposits on said capillary tube, the improvement comprising, the addition of an injector sheath tube mounted concentrically about said capillary tube and extending to a length such that the open end of said injector sheath tube is parallel with the open end of said capillary tube; opposite to said open end said injector sheath tube is joined to the base of said inner tube such that the flow of said argon plasma is directed through the narrow confines of the space between said injector sheath tube and said capillary tube in such a manner as to concentrate said flow of said argon plasma gas so that said flow deliberately makes contact with the surface of said plasma fireball at the point of injection of a sample gas.

2. The improvement defined in claim 1 in which said flow of said argon plasma gas established by said injector sheath tube alters the surface of said plasma fireball and facilitates the penetration of molecular sample gases such as air or flue gas into said argon plasma fireball.

3. The improvement defined in claim 2 in which said flow of said argon plasma assures complete penetration of said molecular sample gas introduced at optimum flow rates of about 0.3–0.6 liters per minute which preserves residence time in said plasma fireball for said molecular sample gas to effect efficient vaporization and excitation of entrained metals.

4. The improvement defined in claim 2 in which said molecular sample gas is mixed air (nitrogen, oxygen), argon and air-entrained metals.

5. The improvement defined in claim 2 in which said argon plasma gas is at a flow rate of about 0.7–1.0 liters per minute.

6. The improvement defined in claim 2 in which said molecular sample gas includes air or combustor flue gas.

7. The improvement defined in claim 2 in which said injector sheath tube has an inner diameter of about 7 mm and said capillary tube has an outer diameter of about 4 mm to create an annulus of about 1.5 mm.

\* \* \* \* \*